United States Patent
Gary, Jr. et al.

(10) Patent No.: US 6,640,246 B1
(45) Date of Patent: Oct. 28, 2003

(54) INTEGRATED COMPUTERIZED MATERIALS MANAGEMENT SYSTEM

(75) Inventors: Wyndham Fairchild Gary, Jr., Whitefish Bay, WI (US); Thomas Gilbert, Waukesha, WI (US); Donald M. Trombatore, Milwaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/398,180

(22) Filed: Sep. 17, 1999

(51) Int. Cl.7 .......................................... G06F 15/173
(52) U.S. Cl. ................................. 709/223; 709/224
(58) Field of Search ................................ 709/200, 226, 709/224, 229, 223

(56) References Cited

U.S. PATENT DOCUMENTS

| | | | |
|---|---|---|---|
| 4,715,385 A | | 12/1987 | Cudahy et al. |
| 4,895,161 A | | 1/1990 | Cudahy et al. |
| 5,119,104 A | | 6/1992 | Heller |
| 5,291,399 A | * | 3/1994 | Chaco ............................ 705/3 |
| 5,319,363 A | * | 6/1994 | Welch et al. .......... 340/825.36 |
| 5,434,775 A | * | 7/1995 | Sims et al. ..................... 705/8 |
| 5,689,242 A | * | 11/1997 | Sims et al. ................. 340/652 |
| 5,761,432 A | * | 6/1998 | Bergholm et al. .......... 709/226 |
| 6,269,392 B1 | * | 7/2001 | Cotichini et al. ........... 709/229 |

* cited by examiner

Primary Examiner—Ayaz Sheikh
Assistant Examiner—Philip B. Tran
(74) Attorney, Agent, or Firm—Foley & Lardner; Peter J. Vogel; Michael A. Della Penna

(57) ABSTRACT

A resource management system is described. The resource management system includes a resource manager in communication with two networks, including one network having a plurality of patient monitoring devices connected thereto. The resource manager allows automatic location of patient monitors, automatic status notification as to the status of patient monitors and automatic use metering of patient monitor usage, among other functions.

47 Claims, 1 Drawing Sheet

INTEGRATED COMPUTERIZED MATERIALS MANAGEMENT SYSTEM

FIELD OF THE INVENTION

The disclosure relates to a system for managing resources used when providing continuous physiological condition monitoring of a patient. Further, the present invention relates to a system for providing automatic asset location, notification of patient discharge, and usage and maintenance of metering, monitoring, and sensing equipment.

BACKGROUND OF THE INVENTION

In hospitals or other healthcare settings, it is frequently necessary to observe critical physiological conditions of a patient, such as temperature, breath rate, pulse, blood pressure, electrocardiogram (ECG) data, and cardiac output. Further, other conditions may be observed, depending on the injury or illness of the patient.

The physiological condition data is obtained by sensors applied to the patient. These sensors may be connected to a monitor by cables. The monitor may be mounted beside the patients bed and may be connected to a central communications system for recording and monitoring the data. Metering units are also commonly used in healthcare settings to provide specified dosages of medication or fluids to patients. Hospitals or healthcare centers often have hundreds or even thousands of patient meters, monitors, and sensor modules. Typically, each meter, monitor, or sensor module is an electronic device connected to a hospital monitoring network. Such a hospital monitoring network typically has at least one central information center or central communications center connected thereto. The central information center or central communications center allows attendants to view patient data either real time or stored.

A work order system may be used to keep track of scheduled maintenance of the patient monitors or sensors, based on length of ownership of the meters, sensors, or monitors. However, the meters, sensors, and monitors are not continuously used. Meters, sensors, or monitors are continuously being connected and disconnected from the hospital monitoring network and the patient and lay idle or are transferred to a different location in the healthcare facility.

The work order system does not keep track of when a meter, sensor, or monitor is in use, where a meter, sensor, or monitor is in use, how long a meter, sensor, or monitor is in use, or the current status of a meter, sensor, or monitor.

Many of the meters, monitors, and sensors used are self-contained units having microprocessor devices that carry out instructions embedded in software. These units often require periodic software upgrades so that the monitors and sensors can facilitate doctors and medical staff to provide the best possible healthcare available using up to date metering, monitoring, and sensing equipment. When a meter, monitor, or sensor is scheduled for maintenance, the status of that meter, monitor, or sensor is not available to the work order system. Therefore, a maintenance technician may be dispatched to perform scheduled maintenance and arrive at the location of the meter, monitor, or sensor that is schedule for maintenance only to find that it is being used by a patient or that it is in another part of the hospital. Dispatching technicians to perform scheduled maintenance or scheduled upgrades when a meter, monitor, or sensor is not available is an unnecessary expense incurred by the healthcare facility. Furthermore, the difficulties that technicians face in locating meters, monitors, and sensors within a healthcare facility also causes lost man-hours by the technician and further unnecessary expense to be incurred by the healthcare facility.

Furthermore, although software upgrades are periodically available, it has conventionally been problematic to track what software upgrades have been performed and when. It has also been problematic to schedule periodic software upgrades.

Therefore, there is a need for an automated system that provides meter, monitor, or sensor maintenance information to technicians to provide schedule maintenance. Also, there is a need for an automatic system that schedules maintenance based on hour meter data rather than length of ownership data. Further, there is a need for an automated maintenance system that provides the status of devices and communicates their availability to a work order system and/or maintenance technicians. Further still, there is a need for an automated system that provides for locating equipment on a hospital network. Further still, there is a need for an automated system that automatically determines the software upgrades that have or have not been made. Further still, there is a need for an automated system of providing usage information to work order system. Further still, there is a need for an automated system which creates a record of when a new meter, monitor, or sensor is plugged into the hospital monitoring network.

SUMMARY OF THE INVENTION

An exemplary embodiment relates to a resource management system. The resource management system includes a first communications network, having a plurality of communication ports. The resource management system also includes a plurality of electronic devices configured to be in communication with the first communications network, each electronic device has an identifier associated therewith. The resource management system also includes a resource manager that is configured to be in communication with the first network and is configured to read the identifier of the electronic devices in communication with the first communications network.

Another embodiment relates to a hospital monitoring network. The hospital monitoring network includes a plurality of communication ports coupled to the hospital monitoring network, each communication port has a location identifier associated therewith. The hospital monitoring network also includes a plurality of hospital devices configured to be in communication with the hospital monitoring network. Each hospital device has an identifier associated therewith. The hospital monitoring network further includes a server configured to be in communication with the hospital monitoring network. The server is configured to read the identifiers of the hospital devices in communication with the hospital monitoring network via at least one of the communication ports. The server is configured to read the location identifiers of at least one communication port to which the electronic devices are in communication with.

Yet another embodiment relates to a resource management system. The resource management system includes a first communications network and a second communications network. The resource management system includes a plurality of monitors selectively coupled to at least one of the first communications network and the second communications network. The resource management system further includes a resource manager in communication with both the first communications network and the second communications network. The resource manager is configured to receive monitor information from at least one of the first communications network and the second communications network. The resource manager is configured to receive location information representative of the location of the monitors that are coupled to either of the first communications network and the second communications network.

Still yet, another embodiment relates to a resource management system. The resource management system includes a first means for communicating and a second means for communicating. The resource management system also includes a plurality of electronic devices selectively coupled to at least one of the first communicating means and the second communicating means. The resource management system also includes a means for managing resources in communication with both the first communicating means and the second communicating means. The managing means is configured to receive location identifiers and electronic device information from at least one of the first communicating means and the second communicating means.

Further still, another embodiment relates to a method of managing assets. The method includes communicating electronic device information over a first communications network. The method also includes receiving electronic device information from the first communications network by a resource manager. Further, the method includes communicating location information representative of the location of the electronic device over the first communications network and receiving location information from the first communications network by a resource manager.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE PREFERRED EMBODIMENTS

Figure 1:
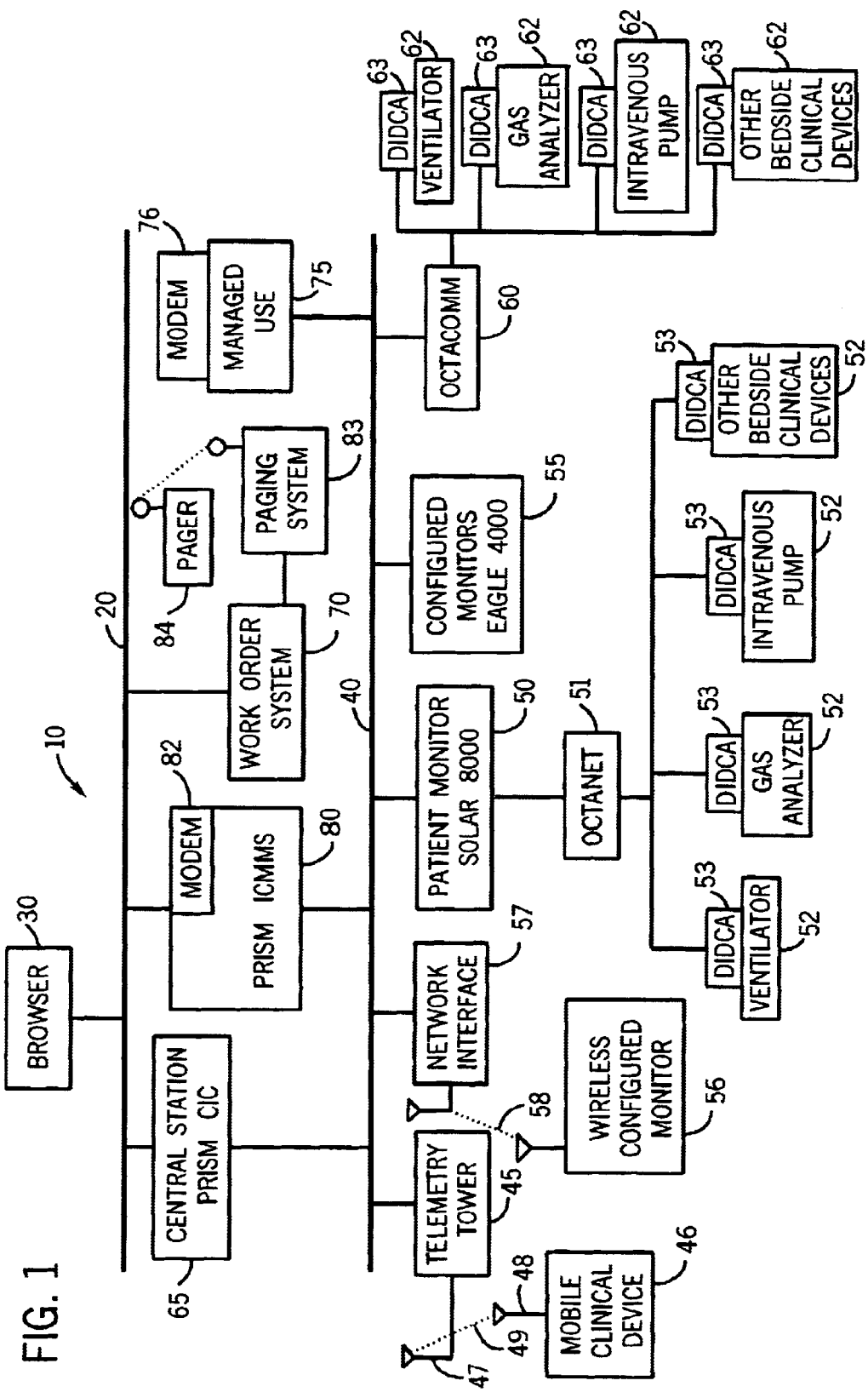
FIG. 1 is a block diagram of an exemplary embodiment of a healthcare monitoring network.

Referring to FIG. 1, a block diagram of a hospital monitoring network 10 is depicted. Hospital monitoring network 10 includes a hospital enterprise network 20 which may be an intra hospital communications network or external communications network that is in communication with a plurality of other hospitals, service providers, equipment vendors, or other personnel (including, but not limited to, off-site doctors or healthcare technicians) or entities requiring information available from or provided by a hospital. The information communicated on hospital enterprise network 20 may be retrieved by a user through a browser 30, such as a web browser or other network user interfaces.

Hospital monitoring system 10 preferably includes a hospital monitoring network 40. Hospital monitoring network 40 may be, in a preferred embodiment, an inter hospital network such as the GE Marquette Unity Network® available from GE Marquette Medical, Inc., Milwaukee, Wis., or any other of a variety of mission critical networks. Further, hospital monitoring network 40 is a communications network that may be an Ethernet network supporting transmission control protocol/internet protocol (TCP/IP) standards or any other applicable communication protocols. In a preferred embodiment, hospital monitoring network 40 may be used to share clinical information between different parts of a healthcare facility, such as, but not limited to cardiology, patient monitoring, hospital information, and laboratory equipment. Further, in a preferred embodiment, hospital monitoring network 40 may be built using industry-standard equipment, for example IEEE 802.3 (Ethernet) cabling. A plurality of electronic devices and more particularly hospital devices such as, but not limited to, computers, patient monitors, patient meters, and patient sensors, and other communication and interfacing devices.

Hospital monitoring network 40 is preferably configured to be connected with a plurality of communication devices, such as, but not limited to, a telemetry tower 45, a patient monitor 50, a configured monitor 55, and a monitoring interface device 60. Further, in a preferred embodiment, computer and computer server devices such as a central station 65, a work order system 70, a managed use system 75 and a resource manager 80 may be in communication with hospital monitoring network 40. Further, any number of or variety of computer systems may be coupled to and in communication with hospital monitoring network 40.

Telemetry tower 45 preferably has a plurality of receivers. In a preferred embodiment, telemetry tower 45 has 16 receivers. Further, in a preferred embodiment telemetry tower 45 may be an APEX® telemetry transmitter available from GE Marquette Medical Systems, Inc. Associated with telemetry tower 45 is an antenna 47 configured to transmit and receive preferably radio frequency (RF) or ultra high frequency (UHF), or any other appropriate electromagnetic signal 49. Telemetry tower 45 is therefore in communication with a plurality of mobile clinical devices 46, each mobile clinical device has an antenna 48 associated therewith configured to transmit and receive signals 49 to and from telemetry tower 45. Therefore, signals to and from mobile clinical device 46 are communicated on hospital monitoring network 40 through telemetry tower 45.

Patient monitor 50 may be coupled to hospital monitoring network 40. Patient monitor 50 may be a patient monitor that tracks and displays patient sensor and monitor data for a single patient. Patient monitors of this type include but are not limited to the Solar 8000 available from GE Marquette Medical Systems, Inc.

Patient monitor 50 may be coupled to and in communication with a multiplexing device 51 such as Octanet available from GE Marquette Medical Systems, Inc. Multiplexing device 51 provides a plurality of ports, preferably eight (8) ports whereby a plurality of patient monitoring devices may be coupled thereto. Multiplexing device 51 acts to bring data from a plurality of patient monitoring and sensing devices into one device to be communicated to a patient monitor 50, or the like.

Patient monitor 50 may be configured to include a transportation acquisition module (TRAM®) available from GE Marquette Medical Systems, Inc. that is configured to travel with the patient when the patient moves throughout the hospital or healthcare facility. Multiplexing device 51 has a plurality of ports which are preferably coupled to the plurality of patient meters, monitors, or sensors 52 which may be any of a plurality of patient metering, monitoring, and sensing devices including but not limited to ventilators, gas analyzers, intervenes pumps, other bedside clinical devices, or other devices including those which are not necessarily medical devices per se.

Each device 52 preferably has a device identification cable adapter (DIDCA™) 53 coupled thereto. Each DIDCA 53 is configured to return a unique digital identifiers (e.g., identification number) that is unique to each device 52. In the present embodiment, the number is unique to each DIDCA and is correlated to devices 52. Each DIDCA automatically identifies a device as soon as it is connected to the network.

Each device 52 is configured to retrieve information directly or indirectly from patient clinical bedside devices. Such information is communicated through DIDCA 53 to multiplexing device 51 along with the unique identification number associated with device 52. Multiplexing device 51 collects data from the plurality of devices 52 and communicates that information to a patient monitor 50. Patient monitor 50, preferably has a unique Ethernet address and is configured to communicate monitor information along hospital monitoring network 40.

Configured monitors 55 may also be connected and in communication with hospital monitoring network 40. Configured monitors are preferably Eagle 4000 or Eagle 3000 configured monitors available from GE Marquette Medical Systems, Inc., or possibly other configured monitors that are capable of communicating patient information along the hospital monitoring network 40. Configured monitors 55 are full featured vital sign monitors that offer software and hardware options which allow it to be configured to meet the needs of specific care units. For example, in a preferred embodiment configured monitor 55 may be used to monitor basic standard of care parameters and can be expanded to include a plurality of other parameters such as, but not limited to invasive pressures, thermal dilution, cardiac output, electrocardiogram analysis among other parameters. In an alternative embodiment, configured monitors may be wireless configured monitors 56 in communication with a network interface, such as Ethernet interface 57, and communicating via a wireless Ethernet signal 58.

A network interface device 60 may also be coupled to and in communication with hospital monitoring network 40. Network interface device 60, like configured monitors 55, patient monitor 50 and telemetry tower 45, has its own unique Ethernet address used for communicating along hospital monitoring network 40. Network interface device 60 much like multiplexing device 51 has a plurality of communication ports, in a preferred embodiment eight (8) ports. In a preferred embodiment, network interface device 60 may preferably be an Octacomm, available from GE Marquette Medical Systems, Inc. Network interface device 60 serves as an interface between hospital monitoring network 40 and up to eight (8) bedside devices, such as but not limited to ventilators, infusion pumps, and vital sign monitors. Network interface device 60 acts to bring data together from a plurality of patient monitoring devices 62. Patient monitoring devices 62 may be the same as or different than devices 52 that are connected to multiplexing device 51. In a preferred embodiment, devices 62 have DIDCAs 63 coupled to and associated with devices 62. Therefore, each device 62 has associated therewith by DIDCA 63 a unique identification number. Similar to devices 52, patient monitoring information and data is collected via devices 62 and broadcast through DIDCAs 63 to network interface device 60 patient data is then collected and brought together in network interface device 60 where it can be communicated to hospital monitoring network 40 and associated with the unique Ethernet address of network interface device 60.

A central station 65 may be coupled preferably to both hospital monitoring network 40 and hospital enterprise network 20. Central station 65 may preferably be a PRISM™ clinical information center (CIC) available from GE Marquette Medical Systems, Inc. CIC is a PC based central station running under Windows NT®. The CIC provides centralized monitoring of patients that are connected to Solar® monitors, Eagle® monitors and APEX® telemetry transmitters. CIC may be configured to display up to four (4) real-time wave forms per patient for up to sixteen (16) patients. A display window is provided on the CIC for each patient. The display window shows wave forms and vital information in digital form, including, but not limited to patient name, bed number, arrhythmia messages, alarms on/off, alarm message line, heart rate, PVC count, transmitter number, ECG lead label, pacemaker status, ST measurement, graph status, additional parameter numerics from Solar or Eagle monitors and date/time. Any number of central stations may be in communication with hospital monitoring network 40. Central station 65 retrieves information communicated along hospital monitoring network 40 from any of the number of monitors, sensors and devices that are in communication with hospital monitoring network 40. Central station 65 has the ability to display, record, and/or communicate any of the information communicated along the network. For example, a central station 65 may be used in a certain hospital section, department, or ward, so that a plurality of patients can be simultaneously monitored at a centralized location, such as, but not limited to a nurses station.

Optionally a managed use server or computer system 75 may be coupled to and in communication with hospital monitoring network 40. Managed use system 75 further includes a modem 76 coupled thereto for communications across a standard telephone line or other communication lines such as coaxial lines, fiberoptic lines, cellular, radio or satellite signal lines. Managed use system 75 is preferably used to communicate with a hospital equipment provider, or a service provider for a hospital equipment supplier. Managed use system 75 makes it possible for a hospital or healthcare facility to use equipment strictly on a pay-per-use system, whereby the hospital pays a medical equipment provider only for the time for which the medical equipment is being used. Managed use system 75 collects information from the hospital monitoring network communicates that information via modem 76 to a service provider who processes the information and sends out a bill, based on the information collected, to the hospital.

A work order system 70 database may be coupled to the hospital enterprise network 20. In a preferred embodiment, work order system 70 is WOSYST® for Windows® available from St. Croix Systems, Inc., St. Croix Falls, Wis. Work order system 70 is configured to schedule maintenance based on length of ownership of devices such as telemetry tower 45, patient monitor 50, configured monitor 55, network interface device 60, Octanet 51, monitors or sensors 52 and monitors or sensor 62, and any other devices that may be coupled to network 40. Data input to work order system 70 is conventionally input by hand using little or no automation. Work order system 70 provides a capital equipment database system however work order system 70 does not provide real-time location of and management of hospital assets.

In a preferred embodiment, a resource manager 80 is coupled to both hospital monitoring network 40 and hospital enterprise network 20. Resource manager 80 is preferably a PRISM® integrated computerized maintenance management system (ICMMS) available from GE Marquette Medical Systems, Inc. In a preferred embodiment the ICMMS software is configured to run under Windows NT®. Resource manager 80 is configured to reduce the time and complexity associated with preventive and schedule maintenance of patient monitoring equipment. Resource manager 80, which in one embodiment is a computer server running ICMMS software, preferably provides automatic asset location, notification of patient discharge and use metering of equipment that is connected to the hospital monitoring network 40. In a preferred embodiment, each patient room, or other location throughout the hospital or healthcare facility have communication ports. The communication ports are configured to be connected to hospital monitoring network 40 and are further configured to connect to and be in communication with any of a plurality of patient devices including but not limited to telemetry tower 45, patient monitor 50, multiplexing device 51, patient monitor and sensing devices 52, configured monitors 55, network interface device 60, patient monitoring devices 62. In a preferred embodiment, each communication port has digital information (e.g., location tag or location identification) associated therewith for communicating across network 40.

Resource manager 80 may preferably be configured to identify the first time that any new equipment coming into the hospital is plugged into hospital monitoring network 40. Resource manager 80 therefore keeps a record of the new equipment thereafter. When it is time for equipment to undergo routine preventive maintenance, a technician is alerted that maintenance is needed and further is informed of the location of the specific device in the hospital by way of a location identifier associated with the communication port with which the device communicates. Furthermore, resource manager 80 may identify if the device needing maintenance is being used by a patient, and when that patient will be discharged or no longer needs to use the device therefore freeing up its availability for service, this saves precious work time of technicians.

Resource manager 80 provides automatic asset location. In hospitals and healthcare facilities, equipment is often moved from its assigned location thereby causing time consuming delays as technicians search for the device throughout the hospital or healthcare facility. Resource manager 80 allows users to provide a query to the system to ascertain the exact location, and the current software level of most devices connected to hospital monitoring network 40.

In a preferred embodiment, work order system 70 can signal a paging system 83 to notify a technician, carrying a pager 84, when a piece of equipment is schedule for preventive maintenance or to notify him or her when specified equipment is no longer in use by a patient.

Resource manager 80 preferably has a modem 82 coupled thereto. Modem 82 allows a user to dial into and connect with resource manager 80. A user may then be able to view information available through resource manager 80 and in a preferred embodiment a user will be able to view information stored in work order system 70.

Resource manager 80 also facilitates use metering that provides hour meter data, that is data based on the time a particular device has been in use. Not only does this provide for simple pay-for-use accounting, but it also provides for accurate assessment of service requirements for each device thereby providing efficiency in the use of a technician's time as compared with a conventional calendar-based maintenance schedule.

Resource manager 80 preferably receives device information including, but not limited to location, unique identification number (physical Ethernet address, a serial number, or a DIDCA number) hardware revisions, software revisions, software error logs, device usage (patient admitted), and other device status like internal temperatures, etc.

Resource manager 80 provides automation of scheduled maintenance and other tasks including, but not limited to, device monitoring, providing software and hardware upgrades, and automated pay-per-use billing. Further, resource manager 80 is able to communicate across hospital enterprise network 20 and provide data directly to work order system 70 therefore providing work order system 70 with an automated method of gathering input data. Furthermore, resource manager 80 allows hospital equipment to be readily located, or if no longer on the network, resource manager 80 can provide information as to where and when the equipment was last used. This information may be provided to a user through a browser such as browser 30 in communication with hospital enterprise network 20, or in an alternative embodiment coupled to and in communication with hospital monitoring network 40.

While the preferred embodiment refers to a resource manager coupled to two communication networks, the present invention may also be applied to a resource manager coupled to a single communications network.

Further, while the preferred embodiment refers to patient meters, monitors, or sensors, this phrase is to be interpreted broadly. The embodiment can encompass those situations in which any electronic device is coupled to and in communication with a communications network.

Further still, those who have skill in the art will recognize that the present invention is applicable with many different hardware configurations software architectures, communications protocols, and organizations or processes.

While the detailed drawings, specific examples, and particular formulations given describe preferred embodiments, they serve the purpose of illustration only. The materials and configurations shown and described may differ depending on the chosen performance characteristics and physical characteristics of the communication networks. For example, the type of communications network or communication protocols used may differ. The systems shown and described are not limited to the precise details and conditions disclosed. Furthermore, other substitutions, modifications, changes, and omissions may be made in the design, operating conditions, and arrangement of the preferred embodiments without departing from the spirit of the invention as expressed in the appended claims.

What is claimed is:

1. A resource management system comprising:

a first communications network, having a plurality of communication ports;

a plurality of electronic devices configured to be in communication with the first communications network, each electronic device having an identifier associated therewith, each identifier being any of a plurality of types of identifiers including an address, a device identification number, a device serial number, and a unique digital identifier, each electronic device being configured to provide clinical information to the first communications network;

a resource manager configured to be in communication with the first network, the resource manager configured to handle each different type of identifier and the resource manager configured to read each identifier of the electronic devices in communication with the first communications network, the resource manager receiving time of use metering and status information from each of the electronic devices;

a second communications network, wherein the resource manager is in communication with the second communications network; and a work order system in communication with at least one of the first communications network and the second communications network, wherein the work order system issues work orders for maintenance based on time of use metering and status information gathered by the resource manager.

2. The resource management system of claim 1 wherein each communication port has a location identifier associated therewith.

3. The resource management system of claim 2 wherein the resource manager is configured to read the location identifier of the ports through which the electronic devices in communication with the first communications network are communicating.

4. The resource management system of claim 1 further comprising:
a user interface device in communication with at least one of the first communications network and the second communications network.

5. The resource management system of claim 1 further comprising:
a central data center, configured to be in communication with the first communications network.

6. The resource management system of claim 5 wherein the central data center is configured to display data from at least one of the plurality of electronic devices.

7. The resource management system of claim 1 wherein the first communications network is an inter hospital monitoring network.

8. The resource management system of claim 1 wherein some of the electronic devices are one of patient meters, patient monitors, and patient sensors.

9. A hospital monitoring network comprising:
a plurality of communication ports coupled to the hospital monitoring network, each communication port having a location identifier associated therewith;
a plurality of hospital devices configured to be in communication with the hospital monitoring network, each hospital device having an identifier associated therewith, the identifier being any of a plurality of types including an address, a device identification number, a device serial number, and a unique digital identifier, each hospital device being configured to provide clinical information to the hospital monitoring network;
a server configured to be in communication with the hospital monitoring network, the server configured to read each identifier of the hospital devices in communication with the hospital monitoring network via at least one of the communication ports and the server configured to read the location identifiers of at least one communication port to which the hospital devices are in communication with, the server configured to identify each device based on each different type of identifier, the server providing location information relating to location of the plurality of electronic devices and the server providing time of use metering of the plurality of electronic devices, the time of use metering indicating the length of time for which each device has been in use and the server providing status information for the plurality of electronic devices; and
a work order system in communication with the hospital monitoring network,
wherein the work order system issues work orders for maintenance based on time of use metering and status information gathered by the server.

10. The hospital monitoring network of claim 9 wherein at least some of the plurality of hospital devices is in communication with an interface module, the interface module being coupled to the hospital monitoring network.

11. The hospital monitoring network of claim 9 wherein the server is coupled to an external network.

12. The hospital monitoring network of claim 9 wherein the hospital monitoring network is an Ethernet.

13. A resource management system comprising:
a first communications network;
a second communications network;
a plurality of monitors selectively coupled to at least one of the first communications network and the second communications network, each monitor device being configured to provide clinical information to at least one of the first communications network and the second communications network;
a resource manager in communication with both the first communications network and the second communications network, the resource manager configured to receive monitor information from at least one of the first communications network and the second communications network and the resource manager configured to receive location information representative of the location of the monitors that are coupled to either of the first communications network and the second communications network; and
a work order system in communication with at least one of the first communications network and the second communications network,
wherein the monitor information includes monitor identification information from each monitor, each monitor using any of more than one type of monitor identification information including a device identification number, a device serial number, an address, and a unique digital identifier, and the monitor information including time of use metering information, the time of use metering information indicating the length of time for which each monitor has been in use and status information and the work order system issues work orders for maintenance based on time of use metering and status information gathered by the resource manager.

14. The resource management system of claim 13 wherein the monitor information includes a monitor identification.

15. The resource management system of claim 13 wherein the monitor information includes monitor software upgrade information.

16. The resource management system of claim 13 wherein the resource manager facilitates updating hour meter data.

17. The resource management system of claim 13 wherein the monitor information includes status data.

18. The resource management system of claim 13 further comprising:
a user interface in communication with at least one of the first communications network and the second communications network.

19. A resource management system comprising:
a first means for communicating;
a second means for communicating;
a plurality of electronic devices selectively coupled to at least one of the first communicating means and the second communicating means, each electronic device being configured to provide clinical information to at least one of the first means for communicating and the second means for communicating;
a means for managing resources in communication with both the first communicating means and the second communicating means, the managing means configured to receive location identifiers and electronic device information from at least one of the first communicating means and the second communicating means, the electronic device information including any of a device identification number, a device serial number, an address, and a unique digital identifier, and the device information including time of use metering information, the time of use metering information indicating the length of time for which each device has been in use, and status information for the plurality of electronic devices; and a work order system in communication with at least one of the first communications network and the second communications network, wherein the work order system issues work orders for maintenance based on time of use metering and status information gathered by the resource manage.

20. The resource management system of claim 19 wherein the electronic device information includes an electronic device identifier.

21. The resource management system of claim 19 wherein the electronic device information includes electronic device software and hardware revision information.

22. The resource management system of claim 19 wherein the first communicating means is a local communications network.

23. The resource management system of claim 19 wherein the second communicating means is an external communications network.

24. The resource management system of claim 19 further comprising an interface means in communication with at least one of the first communicating means and the second communicating means.

25. The resource management system of claim 19 wherein the work order system is configured to communicate with a paging system.

26. The resource management system of claim 25 wherein the work order system is configured to communicate with the paging system based upon electronic device information.

27. The resource management system of claim 19 wherein the electronic device information includes a patient status indicator.

28. The resource management system of claim 19 wherein the managing means is a computer server.

29. The resource management system of claim 19 wherein the managing means is configured to provide location information of the plurality of electronic devices.

30. The resource management system of claim 19 wherein the managing means is configured to provide automated notification of the status of the plurality of electronic devices for a plurality of predetermined events.

31. The resource management system of claim 19 wherein the managing means is configured to provide automated use metering for each of the plurality of electronic devices.

32. The resource management system of claim 19 wherein the managing means is configured to communicate electronic device information to a service provider over the second communicating means.

33. The resource management system of claim 19 wherein the managing means is configured to communicate electronic device usage information to a service provider over the second communicating means.

34. A method of managing assets, comprising:
communicating electronic device information over a first communications network;
communicating clinical information over the first communications network;
receiving electronic device information from the first communications network by a resource manager, the electronic device information including any of a device identification number, a device serial number, an address, and a unique digital identifier, and the device information including time of use metering information, the time of use metering information indicating the length of time for which each device has been in use;
communicating location information, representative of the location of the electronic device, over the first communications network; and
receiving location Information from the first communications network by a resource manager;
receiving device availability information by the resource manager, over the first communication network;
communicating time of use and availability information to a work order system; and
providing a notification when an electronic device is scheduled for maintenance and when the electronic device is available.

35. The method of claim 34 further comprising:
querying the resource manager to ascertain the location of an electronic device.

36. The method of claim 34 further comprising:
providing a notification when an electronic device is scheduled for maintenance.

37. The method of claim 34 comprising:
broadcasting a paging signal representative of the notification.

38. The method of claim 34 further comprising:
communicating electronic device usage information over the first communications network; and
receiving the electronic device usage information from the first communications network by the resource manager.

39. The method of claim 38 further comprising:
communicating the electronic device usage information to a service provider.

40. The method of claim 38 further comprising:
storing the electronic device usage information in a database.

41. The method of claim 34 further comprising:
communicating electronic device information through a device identification cable adapter.

42. The method of claim 34 further comprising:
communicating electronic device information through a network interface device.

43. The method of claim 34 further comprising:
communicating electronic device information through a wireless communications device.

44. The method of claim 34 further comprising:
communicating electronic device information over a telemetry system.

45. The method of claim 34 further comprising:
communicating electronic device information to a work order system.

46. The method of claim 34 further comprising:
communicating electronic device information over a second communications network.

47. The method of claimer 34 further comprising:
communicating electronic device usage information to a second communications network.

* * * * *

UNITED STATES PATENT AND TRADEMARK OFFICE
CERTIFICATE OF CORRECTION

PATENT NO. : 6,640,246 B1
DATED : October 28, 2003
INVENTOR(S) : Wyndham Fairchild Gary, Jr. et al.

It is certified that error appears in the above-identified patent and that said Letters Patent is hereby corrected as shown below:

<u>Column 12,</u>
Line 13, please replace "Information" with -- information --.

Signed and Sealed this

Thirteenth Day of April, 2004

JON W. DUDAS
*Acting Director of the United States Patent and Trademark Office*